United States Patent [19]
Wilmsmann

[11] Patent Number: 5,229,105
[45] Date of Patent: Jul. 20, 1993

[54] MULTI-ACTIVE SKIN PREPARATION

[75] Inventor: Hermann Wilmsmann, Monschau, Fed. Rep. of Germany

[73] Assignee: Donald Basiliere, Haverhill, Mass.

[21] Appl. No.: 864,144

[22] Filed: Apr. 6, 1992

Related U.S. Application Data

[63] Continuation of Ser. No. 422,696, Oct. 17, 1989, abandoned, which is a continuation-in-part of Ser. No. 868,315, May 28, 1986, abandoned.

[51] Int. Cl.$^5$ .......................... A61K 7/40; A61K 7/48; A61K 9/10
[52] U.S. Cl. .................................. 424/59; 514/844; 514/847; 514/865; 514/938; 514/941; 514/943
[58] Field of Search ............... 514/941, 938, 943, 865; 424/59

[56] References Cited

U.S. PATENT DOCUMENTS

| | | | |
|---|---|---|---|
| 2,900,306 | 8/1959 | Slater | 252/122 |
| 4,052,331 | 10/1977 | Dumoulin | 424/184 |
| 4,479,887 | 10/1984 | Seibert | 514/938 |

FOREIGN PATENT DOCUMENTS

| | | | |
|---|---|---|---|
| 675152 | 7/1952 | United Kingdom | 514/943 |

*Primary Examiner*—Dale R. Ore
*Attorney, Agent, or Firm*—Cesari and McKenna

[57] ABSTRACT

A skin preparation offering protection against a variety of irritants (including allergens) is prepared from an oil-in-water emulsion of the cationic type, with a fatty acid mono-ester or di-ester of triethanolamine, or a fatty acid amide of hydroxyethyl-ethylenediamine, as the cation and active barrier ingredient. The resulting emulsion binds strongly to the skin through electrostatic bonding and forms an invisible yet effective barrier that isolates the skin from adversely charged irritants, small organic compounds, irritants of high molecular weight, and irritants of alkaline pH. The skin preparation may incorporate additional active agents, such as sunscreens, antibiotics and other therapeutics, for application of these agents to the skin.

26 Claims, No Drawings

MULTI-ACTIVE SKIN PREPARATION

This is a continuation of Ser. No. 07/422,696, filed Oct. 17, 1989, now abandoned, which was itself a continuation-in-part of Ser. No. 06/868,315, filed May 28, 1986, now abandoned.

FIELD OF THE INVENTION

The invention relates to protective skin preparations, and more particularly, to barrier creams used for protecting the skin against exposure to irritants and allergens during normal working conditions.

BACKGROUND OF THE INVENTION

Industrial contact dermatitis is an important occupational problem that causes much suffering for the afflicted employee and results in loss of productivity for the employer. It is a skin rash that develops from exposure to irritants, such as alkaline detergents or acids, or from exposure to "sensitizing" allergens, such as nickel, poison ivy, or antibiotics. Exposure to the irritants causes lesions that are similar to thermal burns. Exposure to the sensitizing allergens causes an allergic skin reaction that produces redness, swelling and itching. The first contact with such an allergen produces no visible skin reaction, but stimulates certain lymphocytes in a sensitive person to undergo an immunologic change. Upon subsequent exposure to the allergen, these sensitized lymphocytes release irritating substances that produce an inflammatory response in the skin (i.e. redness, swelling and itching). Continued, repeated exposure to these allergens causes the allergic reaction to be more acute and the dermatitis to become more severe.

Both types of dermatitis (irritant and allergic) result in redness, cracking, drying, scaling and blistering of the skin. Some relief of these symptoms is provided by applying soothing or drying lotions to the affected area. Also, topical corticosteroid preparations (which prevent the inflammatory response) may also provide relief. These steroid preparations are not without side effects, however, and should not be used routinely. Accordingly, the only truly effective treatment for contact dermatitis is further avoidance of the causative irritants or allergens. Obviously, therefore, the best cure is avoiding the initial contact with the irritants and/or allergens, i.e. prevention of the condition before it starts.

This goal may be achieved, at least in part, through the application of so-called "barrier creams" that form thin protective coatings on the skin's surface. There are different kinds of barrier creams, each offering protection against a specific class of irritants or allergens.

For example, for protection against powders, dust, dry soils, and highly viscous oils or tars, in which particles lodge in the pores of the skin, creams of oil-in-water emulsions containing inert fillers that protect the pores are used.

For protection against water-based irritants, hydrophobic films prepared from paraffins (petrolatum or beeswax) and/or silicones are used. Many of these hydrophobic films, being water-repellant, permit little, if any, evaporation of sweat from the skin. Accordingly, perspiration can accumulate between the protective film and the skin, thereby loosening the film and reducing its effectiveness. Also, because these hydrophobic films are nonpolar, they have little affinity for the skin, and thus adhere rather poorly to it.

The hydrophobic films can be supplied with emulsifiers to improve skin adhesion and to allow skin respiration. These additives, however, reduce the water repellancy of the film (which is the mode of action of these films), and hence, reduce its effectiveness as a barrier against water-based irritants.

Against organic or oil-based irritants (e.g. acetone, benzene, toluene, alcohol, turpentine, kerosene), hydrophilic substances such as polyethyleneglycols, polyacrylate, starch, gelatin, cellulose ether, or gum tragacanth are used. Also, soap surfactants such as triethanolamine or sodium alginate are used. These films are hydrophilic, and do not inhibit skin respiration. However, excess perspiration may wash off the barrier.

Most of the above films are soluble in either water or solvents, and are thus removed from the skin by washing, by perspiration, or through contact with solvents. Therefore, they require repeated application during a normal workday to ensure complete protection. Also, because of their specificity, they offer only limited overall protection against the wide variety of irritants commonly found in the workplace.

SUMMARY OF THE INVENTION

Accordingly, the present invention aims to provide a protective skin preparation that isolates the skin from contact with a variety of irritants and/or allergens.

A further object of the present invention to provide such a skin preparation that is durable and resilient, and difficult to remove.

Still another object of the present invention is to provide such a preparation that is easy to apply and pleasant to use. Another object of the invention is to provide such a preparation that is non-irritating and non-sensitizing, and does not interfere with normal skin respiration.

Other objects will, in part, be obvious and will, in part, appear hereinafter. The protective skin preparation of my invention is of the general class of oil-in-water emulsions of the cationic type. Specifically, the oil phase of my emulsion comprises a fatty acid monoester or di-ester of triethanolamine, or a fatty acid amide of hydroxyethyl-ethylenediamine, or a mixture of the two. These emulsions, as is typical of oil-in-water emulsions in general, are not greasy or sticky, and remains pliable and elastic even during continued use.

For a fuller understanding of the nature and objects of the invention, reference should be had to the following detailed description.

DESCRIPTION OF THE PREFERRED EMBODIMENTS

The first class of compounds suitable for use in the oil phase of the present invention include mono-esters and di-esters of triethanolamine, of the general forms:

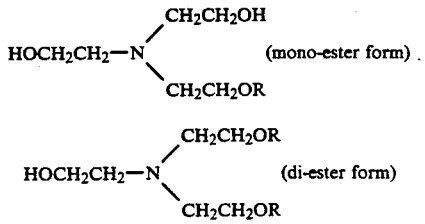

where R is a fatty acid residue containing an alkyl chain that is saturated or unsaturated, with a molecular length between 12 and 20 carbon atoms. Examples of R include:

$C_{11}H_{23}CO$—(lauric acid residue)
$C_{10}H_{19}CO$—(undecylenic acid residue)
$C_{15}H_{31}CO$—(palmitic acid residue)
$C_{17}H_{35}CO$—(stearic acid residue)
$C_{17}H_{33}CO$—(oleic acid residue)
$C_{17}H_{31}CO$—(linoleic acid residue)
$C_{19}H_{39}CO$—(behenic acid residue)

EXAMPLE 1

A specific formulation of the di-ester form of my protective skin preparation based on stearic acid comprises 20% triethanolamine-distearic ester, 3% di-ethyleneglycol-mono-ethylether, 1.83% acetic acid, 74.17% de-ionized water, and 1% perfume oil.

To make the above formulation, an aqueous phase and an oil phase are prepared separately. In a first vessel, 75 g de-ionized water and 1.83 g acetic acid are added. The vessel (and its contents) are heated to 80° C., with mixing, forming the aqueous phase. To a second vessel is added 20 g triethanolamine-di-stearic acid ester (solid), 3 g di-ethyleneglycol-mono-ethylether (solvent), and 1 g perfume oil. The contents of the second vessel are also heated to 80° C., with constant mixing. At this elevated temperature, the solid triethanolamine-di-stearic ester melts in the solvent, forming the "oil" phase. The heated oil phase is then poured slowly into the heated aqueous phase, with constant stirring, forming an oil-in-water emulsion (the solvent acts as the emulsifying agent). The emulsion is then cooled, also with constant stirring, until the temperature falls to below 45° C. The cooled emulsion may be applied to any skin area that is clean and dry. Excess may then be wiped or washed away, and after the solvent evaporates, a dry, protective, invisible "membrane" barrier remains.

Other oil-in-water emulsions may be formulated according to the procedure described above. As described below, esters of triethanolamine and other fatty acids, both saturated (e.g. palmitic) and unsaturated (e.g. oleic acid, linoleic) may be substituted. Also, other solvents and acids may be used, provided they are harmless to the skin and stabilize the emulsion. For example, mild acids, such as citric acid, formic acid and even dilute hydrochloric acid may be substituted for acetic acid in the formulation. The solvent must also act as an emulsifying agent.

Furthermore, the weight-percentage of the constituents may vary from the specific example given above. The triethanolamine-fatty acid ester content of an effective barrier cream may range from 2% to 30% of the total weight. The solvent content may range from 0% to 10%, and the water content may range from 50% to 98%. Also, the pH range may vary from 3 to 7.

EXAMPLE 2

Another formulation of the di-ester form of my protective skin preparation based on lauric acid comprises 20% triethanolamine-lauric ester, 1.5% acetic acid, and 78.5% de-ionized water. This example demonstrates that the solvent may be omitted from the formulation; a smooth cream, rather than an emulsion, will result.

To make the above formulation, an aqueous phase and an oil phase are prepared separately. In a first vessel, 78.5 g de-ionized water and 1.5 g acetic acid are added. The vessel (and its contents) are heated to 80° C., with mixing, forming the aqueous phase. To a second vessel is added 20 g triethanolamine-di-lauric acid ester (solid). The contents of the second vessel are also heated to 80° C., with constant mixing. At this elevated temperature, the solid triethanolamine-di-lauric ester melts, forming the "oil" phase. The heated oil phase is then poured slowly into the heated aqueous phase, with constant stirring. The mixture is then cooled, also with constant stirring, until the temperature falls to below 45° C. The cooled mixture, which appears as a smooth cream, may be applied to any skin area that is clean and dry. Excess may then be wiped or washed away, leaving a dry, protective, invisible "membrane" barrier.

EXAMPLE 3

As previously stated, the method outlined in Example 1 may be adapted for use with other fatty acids. Following the procedures in Example 1, the saturated stearic acid of Example 1 may be replaced with unsaturated oleic acid by altering the proportions to 20% triethanolamine-di-oleic acid ester, 5% diethyleneglycol-mono-ethylether, 1% acetic acid, 73.25% de-ionized water, and 0.75% perfume oil.

The resulting emulsion appears as a heavy milk.

Fatty acid mono-esters of triethanolamine are also suitable for use in the present invention.

EXAMPLE 4

The method outlined in Example 1 may be adapted to produce a triethanolamine mono-ester of lauric acid. Following the procedures in Example 1, triethanolamine-di-stearic ester is replaced with 20% triethanolamine-mono-lauric ester. The remaining proportions are 5% di-ethyleneglycol-mono-ethylether, 1% acetic acid and 74% de-ionized water. The perfume oil has been omitted for this example, as well as several others.

The result is a milky emulsion.

EXAMPLE 5

The method outlined in Example 2 may be adapted to produce a triethanolamine-mono-oleic ester without solvent. Following the procedures in Example 2, saturated lauric acid is replaced with unsaturated oleic acid by altering the proportions to 25% triethanolamine-mono-oleic acid ester, 2.5% acetic acid, 71.5% de-ionized water, and 1% perfume oil.

The resulting preparation is milky in appearance.

The mono- and di-ester forms of the oil phase of my invention may also be combined.

EXAMPLE 6

This example illustrates combination of triethanolamine mono- and di-esters of palmitic acid. 1,2-propyleneglycol has been found to be a preferable solvent in this formulation.

Following the procedures outlined in Example 1, the triethanolamine-distearic ester is replaced with 15% triethanolamine-mono-palmitic ester and 5% triethanolamine-di-palmitic ester, and the di-ethyleneglycol-mono-ethyl ether is replaced with 5% 1,2-propyleneglycol. The remaining proportions are 1% acetic acid and 74% de-ionized water.

The resulting emulsion appears as a smooth cream.

The second class of compounds suitable for use in the oil phase of the present invention include fatty acid amides of hydroxyethyl-ethylenediamine, of the general form:

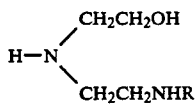

where R is a fatty acid residue containing an alkyl chain that is saturated or unsaturated, with a molecular length between 12 and 20 carbon atoms. Examples of R include:

$C_{11}H_{23}CO$—(lauric acid residue)
$C_{10}H_{19}CO$—(undecylenic acid residue)
$C_{15}H_{31}CO$—(palmitic acid residue)
$C_{17}H_{35}CO$—(stearic acid residue)
$C_{17}H_{33}CO$—(oleic acid residue)
$C_{17}H_{31}CO$—(linoleic acid residue)
$C_{19}H_{39}CO$—(behenic acid residue)

These formulations are prepared in the manner described in Example 1 or 2.

EXAMPLE 7

This example illustrates use of oleic acid amide of hydroxyethyl-ethylenediamine in the oil phase. 1,2-propyleneglycol has been found to be a preferable solvent in this formulation.

Following the procedures outlined in Example 1, the triethanolamine-distearic ester is replaced with 18% oleic acid amide of hydroxyethyl-ethylenediamine, and the di-ethyleneglycol-mono-ethyl ether is replaced with 5% 1,2-propyleneglycol. The remaining proportions are 2.5% acetic acid and 74.5% de-ionized water.

The resulting preparation appears as a milky emulsion.

EXAMPLE 8

Following the procedures in Example 1, the unsaturated oleic acid of Example 7 may be replaced with saturated palmitic acid by altering the proportions to 20% palmitic acid amide of hydroxyethyl-ethylenediamine, 3% 1,2-propyleneglycol, 2.5% acetic acid, and 74.5% de-ionized water.

The resulting preparation appears as a milky emulsion.

The ester and amide forms of the oil-phase component may be combined, as described in the following two examples.

EXAMPLE 9

Following the procedures outlined in Example 1, the triethanolamine-distearic ester may be replaced with 12% triethanolamine-mono-stearic ester and 8% stearic acid amide of hydroxyethyl-ethylenediamine. The remaining proportions are 3% di-ethyleneglycol-mono-ethylether, 1.8% acetic acid and 75.2% de-ionized water.

The resulting preparation appears as a smooth cream.

EXAMPLE 10

Following the procedures outlined in Example 1, the triethanolamine-distearic ester may be replaced with 12% triethanolamine-mono-lauric ester and 8% lauric acid amide of hydroxyethyl-ethylenediamine. The remaining proportions are 3% di-ethyleneglycol-mono-ethylether, 1.8% acetic acid and 75.2% de-ionized water.

The resulting preparation appears as a thin, milky emulsion.

Protective barriers prepared according to the methods outlined above interact strongly with the skin and are not readily removed. This interaction is a result of electrostatic bonding between the positively-charged nitrogen of the triethanolamine or ethylenediamine group and the skin, causing the film to adhere firmly to the outer layer of the skin.

This type of bonding may be compared with the bonding between dyes and the skin. Dye stains cannot be removed with water or washing but disappear after 24 hours along with the shedding of the skin to which it is linked. The strong polar nature of the triethanolamine-fatty acid ester and the ethylenediamine-fatty acid amide causes the fatty acid chains to form a layer on the skin, with the amine groups firmly bonded to the skin, and the fatty acid chains on the outside, thus forming a protective "membrane" barrier.

The protective barrier does not interfere with skin respiration, and is non-irritating and non-sensitizing to the skin. The barrier is invisible, does not evaporate and does not become brittle. It is not easily removed from the skin—even by washing. The effectiveness of the protective skin barrier can only be reduced during the normal work day by continuous abrasion which would remove the outer membrane. In such cases, additional applications would be necessary.

Because of this unique bonding with the skin, it is apparent that the barrier cream may also be utilized for purposes other than protection against irritants and allergens involved in contact dermatitis. For example, the barrier cream may incorporate sunscreens to formulate a water- and swim-resistant tanning preparation. The cream may also be used as a vehicle for application of numerous active ingredients to the skin. Such ingredients are incorporated directly onto the barrier cream and include bacteriocides, fungicides and other therapeutic agents, which serve their intended functions.

The resulting creams may be used for diaper rash ointments or therapeutic skin and hand creams that promote healing of dry, irritated skin. Also, the creams may incorporate cosmetic agents (color, texture, fragrance) for use in the preparation of a wide variety of long-lasting, water-resistant cosmetics.

The protective "membrane" barrier prepared according to the method prevents the passage of high-molecular-weight irritants, both aqueous and organic, and thus protects the skin from the irritating effects of these compounds. Some examples of the high-molecular-weight irritants include animal glues, coal tar, cutting oils, diesel oil, grease, lacquers, rubber compounds, shellac, and waxes. The barrier also protects the skin against dry powders, dirt, dust, or other particles that may become embedded in the pores of the skin. Examples of these particles include dry bleaches, detergents, cleansers, cements, and soils.

The barrier also prevents passage of many organic solutions and solvents that are commonly found in industry, such as acetone, benzene, toluene, alcohol, turpentine, and kerosene, as well as forming a barrier against many aqueous irritants.

The polar nature of the protective skin cream tends to "neutralize" the charged centers on the surface of the skin, thus decreasing the skin's electric potential, and correspondingly decreasing the attraction of charged irritants to the skin surface. Such irritants include analine dyes and salt solutions of antimony, arsenic, barium and chrome.

Because the protective skin cream is mildly acidic, it assists the skin in maintaining its natural acidic pH value, and allows the skin's natural buffering capacity to neutralize alkaline irritants.

The multipurpose barrier cream is not intended as a barrier to solvent absorption of highly absorptive toxic materials through the skin. When exposed to these materials, normal precautions should be exercised.

It can be seen from the foregoing that a protective skin cream can be made that is effective in preventing the skin from exposure to a wide variety of irritants, and thereby protecting it from the detrimental effects of such irritants. The cream binds strongly to the skin, and is durable and resilient. Thus, the objects set forth above, among those made apparent from the preceding description, are efficiently attained. Since certain changes may be made in the above method of production and in the above compositions without departing from the scope of the invention, it is intended that all matter contained in the above description be interpreted as illustrative and not in a limiting sense.

It is also to be understood that the following claims are intended to cover all of the generic and specific features of the invention herein described.

What is claimed as new and desired to be secured by Letters Patent of the United States is:

1. A protective skin preparation prepared from a cationic oil-in-water emulsion wherein the cationic moiety is a mono-ester or di-ester of triethanolamine and a fatty acid, the fatty acid having a molecular length between 12 and 20 carbon atoms, inclusive.

2. The preparation of claim 1 wherein said mono-ester is based on a saturated fatty acid.

3. The preparation of claim 1 wherein said mono-ester is based on an unsaturated fatty acid.

4. The preparation of claim 2 wherein said saturated fatty acid is selected from the group consisting of stearic acid, lauric acid, and palmitic acid.

5. The preparation of claim 3 wherein said unsaturated fatty acid is oleic acid.

6. The preparation of claim 1 wherein said di-ester is based on a saturated fatty acid.

7. The preparation of claim 6 wherein said di-ester is based on an unsaturated fatty acid.

8. The preparation of claim 6 wherein said saturated fatty acid is selected from the group consisting of stearic acid, lauric acid, and palmitic acid.

9. The preparation of claim 7 wherein said unsaturated fatty acid is oleic acid.

10. A protective skin preparation prepared from a cationic oil-in-water emulsion wherein the cationic moiety is a fatty acid amide of hydroxyethyl-ethylenediamine.

11. The preparation of claim 10 wherein said amide is based on a saturated fatty acid.

12. The preparation of claim 10 wherein said amide is based on an unsaturated fatty acid.

13. The preparation of claim 11 wherein said saturated fatty acid is selected from the group consisting of stearic acid, lauric acid, and palmitic acid.

14. The preparation of claim 12 wherein said unsaturated fatty acid is oleic acid.

15. A protective skin preparation comprising a cationic oil-in-water emulsion of
 A. a mono-ester or di-ester of triethanolamine and a fatty acid, the fatty acid having a molecular length between 12 and 20 carbon atoms, inclusive, dissolved in a suitable solvent, emulsified in .
 B. a solution of an acid that is harmless to the skin and water.

16. The preparation of claim 15 wherein said solvent is di-ethyleneglycol-mono-ethylether.

17. The preparation of claim 15 wherein said solvent is 1,2-propyleneglycol.

18. The preparation of claim 15 wherein said mild acid is selected from the group consisting of acetic acid, citric acid, formic acid and dilute hydrochloric acid.

19. A protective skin preparation comprising a cationic oil-in-water emulsion of
 A. a fatty acid amide of hydroxyethyl-ethylenediamine dissolved in a suitable solvent, emulsified in
 B. a solution of an acid that is harmless to the skin and water.

20. The preparation of claim 19 wherein said solvent is di-ethyleneglycol-mono-ethylether.

21. The preparation of claim 19 wherein said solvent is 1,2-propyleneglycol.

22. The preparation of claim 19 wherein said mild acid is selected from the group consisting of acetic acid, citric acid, formic acid and dilute hydrochloric acid.

23. A protective skin preparation prepared by combining, in amounts effective to form an emulsion, ingredients comprising a fatty-acid monoester or diester of triethanolamine, a solvent, a solution of acid that is harmless to the skin and water.

24. A protective skin preparation prepared by combining, in amounts effective to form an emulsion, ingredients comprising a fatty-acid amide of hydroxyethyl-ethylenediamine, a solvent, a solution of acid that is harmless to the skin and water.

25. A method of protecting skin comprising the step of applying thereto a protective skin preparation prepared from a cationic oil-in-water emulsion wherein the cationic moiety is a mono-ester or di-ester of triethanolamine and a fatty acid, the fatty acid having a molecular length between 12 and 20 carbon atoms, inclusive.

26. A method of protecting skin comprising the step of applying thereto a protective skin preparation prepared from a cationic oil-in-water emulsion wherein the cationic moiety is a fatty acid amide of hydroxyethyl-ethylenediamine.

* * * * *